United States Patent
Gerrish

(10) Patent No.: US 8,211,871 B2
(45) Date of Patent: Jul. 3, 2012

(54) TOPICAL SKIN BARRIERS AND METHODS OF EVALUATION THEREOF

(75) Inventor: Donald L. Gerrish, Mankato, MN (US)

(73) Assignee: Coloplast A/S, Humlebaek (DK)

( * ) Notice: Subject to any disclaimer, the term of this patent is extended or adjusted under 35 U.S.C. 154(b) by 1780 days.

(21) Appl. No.: 11/414,770

(22) Filed: Apr. 28, 2006

(65) Prior Publication Data

US 2007/0098657 A1 May 3, 2007

Related U.S. Application Data

(63) Continuation-in-part of application No. 11/262,593, filed on Oct. 31, 2005.

(51) Int. Cl.
*A61K 31/717* (2006.01)
*A61K 8/02* (2006.01)

(52) U.S. Cl. ........... 514/57; 424/401; 514/865; 514/92; 514/63

(58) Field of Classification Search ............ 424/401
See application file for complete search history.

(56) References Cited

U.S. PATENT DOCUMENTS

| | | | |
|---|---|---|---|
| 3,991,741 A | 11/1976 | Northrup, Jr. et al. | |
| 4,080,529 A | 3/1978 | Nagel | |
| 4,087,688 A | 5/1978 | Keller | |
| 4,107,331 A * | 8/1978 | Rosenberg | 514/567 |
| 4,115,701 A | 9/1978 | Guichard | |
| 4,172,273 A | 10/1979 | Schilling et al. | |
| 4,204,881 A | 5/1980 | McGrew | |
| 4,210,391 A | 7/1980 | Cohen | |
| 4,225,786 A | 9/1980 | Perlman | |
| 4,268,752 A | 5/1981 | Herwig et al. | |
| 4,271,359 A | 6/1981 | Herwig et al. | |
| 4,293,196 A | 10/1981 | Hilbert | |
| 4,321,594 A | 3/1982 | Galvin et al. | |
| 4,339,748 A | 7/1982 | Guscott et al. | |
| 4,340,283 A | 7/1982 | Cohen | |
| 4,364,030 A | 12/1982 | Rossin | |
| 4,375,034 A | 2/1983 | Guscott | |
| 4,379,971 A | 4/1983 | Smith et al. | |
| 4,391,495 A | 7/1983 | Mazurkewitz | |
| 4,429,224 A | 1/1984 | Wagli et al. | |
| 5,320,838 A | 6/1994 | Woller | |
| 5,558,872 A * | 9/1996 | Jones et al. | 424/78.03 |
| 5,807,890 A | 9/1998 | Yu et al. | |
| 5,900,245 A | 5/1999 | Sawhney et al. | |
| 6,051,248 A | 4/2000 | Sawhney et al. | |
| 6,074,674 A | 6/2000 | Jay et al. | |
| 6,117,877 A * | 9/2000 | Fogel | 514/266.21 |
| 6,217,894 B1 | 4/2001 | Sawhney et al. | |
| 6,264,963 B1 | 7/2001 | Leifheit et al. | |
| 6,277,364 B1 | 8/2001 | Bucks et al. | |
| 6,352,710 B2 | 3/2002 | Sawhney et al. | |
| 6,403,110 B1 | 6/2002 | Siddiqui et al. | |
| 6,531,147 B2 | 3/2003 | Sawhney et al. | |
| 6,582,683 B2 | 6/2003 | Jezior | |
| 6,706,260 B1 | 3/2004 | Tanaka et al. | |
| 6,809,230 B2 | 10/2004 | Hancock et al. | |
| 6,838,078 B2 | 1/2005 | Wang et al. | |
| 6,849,277 B2 * | 2/2005 | Roig | 424/642 |
| 6,911,211 B2 * | 6/2005 | Eini et al. | 424/401 |
| 7,097,847 B2 * | 8/2006 | Reynolds | 424/401 |
| 7,252,846 B2 | 8/2007 | Dinno | |
| 7,262,181 B2 * | 8/2007 | Zhang et al. | 514/57 |
| 2001/0000728 A1 | 5/2001 | Sawhney et al. | |
| 2002/0025921 A1 | 2/2002 | Petito et al. | |
| 2002/0127266 A1 | 9/2002 | Sawhney et al. | |
| 2003/0077307 A1 | 4/2003 | Klofta et al. | |
| 2003/0091540 A1 | 5/2003 | Ahmad et al. | |
| 2003/0104032 A1 | 6/2003 | Sawhney et al. | |
| 2003/0199440 A1 | 10/2003 | Dack et al. | |
| 2003/0212005 A1 | 11/2003 | Petito et al. | |
| 2005/0026836 A1 | 2/2005 | Dack et al. | |
| 2005/0147679 A1 | 7/2005 | Petito et al. | |
| 2005/0208114 A1 | 9/2005 | Petito et al. | |
| 2006/0263439 A1 | 11/2006 | Fishman | |

OTHER PUBLICATIONS

Flick, E., "Cosmetics Additives: An Industrial Guide",1991, Noyes Publications, pp. 233-235.*
Shah, et al., "Evaluation of Moisture Penetration Through Skin Protectant Barriers by Paper Chromatography", Advances in Wound Care, Jul./Aug. 1995, pp. 20-21, 25, and 27.

* cited by examiner

*Primary Examiner* — Gina C Yu
(74) *Attorney, Agent, or Firm* — Coloplast Corp., Coloplast A/S; Daniel G. Chapik; Nicholas R. Baumann

(57) ABSTRACT

A topical skin barrier for protecting and promoting healing of skin, and for providing comfort to a patient, comprises a semi-solid hydrocarbon, a water-absorbing compound, and a pain relief agent. The topical skin barrier effectively adheres to skin, affords protection from moisture and waste, provides transparency in use, and is anhydrous and therefore is preservative-free. Methods of in vitro evaluation are for (i) a composition's protection from moisture and waste, and (ii) a composition's adhesion to skin.

15 Claims, 2 Drawing Sheets

TOPICAL SKIN BARRIERS AND METHODS OF EVALUATION THEREOF

CROSS REFERENCE TO RELATED APPLICATION

The present application is a continuation-in-part of nonprovisional application Ser. No. 11/262,593 filed on Oct. 31, 2005, the entirety thereof being incorporated herein by reference thereto.

FIELD OF THE INVENTION

The present invention relates generally to topical skin barriers and their evaluation methods. The invention relates specifically to topical skin barriers for protecting and promoting healing of patients' skin, and for providing comfort to patients. The invention also relates specifically to in vitro methods of evaluating the efficacy of topical skin barriers in protecting patients' skin from moisture and waste, and in their adhesion to skin.

BACKGROUND OF THE INVENTION

Topical skin barrier compositions, hereinafter referred to as "topical skin barriers", are known in the medical arts. Topical skin barriers have been used, inter alia, for the treatment of bedridden patients' skin where irritation from moisture, urine, diarrhea, feces, enzymatic drainage, exudate, dust, dirt, and the like (hereinafter, collectively, "moisture and waste") is problematic, painful, and unfortunately commonplace. Patients' skin, regardless of being intact or non-intact, ideally needs to be protected from moisture and waste to prevent skin breakdown, promote healing, and provide comfort.

Ultimately it is the role of topical skin barriers to protect skin exposed to moisture and waste, since enzymes present in waste can quickly lead to skin breakdown. While any topical skin barrier that protects skin from exposure to moisture and waste, acting as a barrier therefrom, may be beneficial, an ability to remain adhered to both intact and non-intact skin is obviously critical to satisfactory performance. Furthermore, known topical skin barriers are often substantially opaque after application to skin which does not allow the condition of the skin to be visually assessed. This can lead to a perceived need to aggressively remove selected portions of the topical skin barrier to visually inspect the skin thereunder; such aggressive removal, in turn, can lead to further injury to the skin.

An example of a known topical skin barrier is disclosed in U.S. Pat. Applic. Pub. No. 2003/0091540 titled "Compositions and Methods for Delivering Antibacterial, Antifungal and Antiviral Ointments to the Oral, Nasal or Vaginal Cavity". Disclosed therein are ointments and methods for treating oral and vaginal fungal and yeast infections. Another is disclosed in U.S. Pat. No. 6,849,277 titled "Composition for Moist Skin". Therein, a composition for treating skin in the presence of excessive moisture is an ointment or paste including zinc oxide, a fungicide, a bactericide, and water-absorbing macromolecular materials in a water-immiscible vehicle.

Although the known compositions have provided, to some degree, acceptable adhesion and barrier properties, they have however been inadequate in several respects. These inadequacies include limitations to certain applications rather than for the skin in general (e.g., the aforecited Pub. No. 2003/0091540) and requirement of a bactericide and a base cream containing water (e.g., the aforecited U.S. Pat. No. 6,849,277). Perhaps even more importantly, known compositions have heretofore not been sufficiently transparent to permit visual inspection.

Therefore, there has existed a long-felt need for a substantially transparent, anhydrous, topical skin barrier for general skin care which is not limited in application to a specific area of a patient's body. Such a product would also optionally include antifungal and pain relief properties. The topical skin barrier would need to adhere well to skin and provide a good barrier in an environment of moisture and waste. Moreover, it would be desirable for such a product to have "detectable transparency", thereby rendering it detectable to an observer while being substantially transparent to permit visual observation of the skin thereunder. There has also existed a long-felt need for a relatively simple and effective in vitro method of evaluating the efficacy of topical skin barriers in protecting patients' skin from moisture and waste, and in their adhesion to skin.

SUMMARY OF THE INVENTION

An object of the present invention is to provide a substantially transparent, anhydrous, topical skin barrier for general skin care which is not limited in application to a specific area of a patient's body.

Another object of the present invention is to provide a substantially transparent, anhydrous, topical skin barrier for general skin care which optionally includes an antifungal property.

Yet another object of the present invention is to provide a substantially transparent, anhydrous, topical skin barrier for general skin care which optionally includes a pain relief agent.

An additional object of the present invention is to provide a substantially transparent, anhydrous, topical skin barrier for general skin care which adheres well to skin and provides a good barrier in an environment of moisture and waste.

A further object of the present invention is to provide a substantially transparent, anhydrous, topical skin barrier for general skin care which has detectable transparency.

A yet further object of the present invention is to provide an anhydrous, preservative-free topical skin barrier that, in turn, provides an environment which is hostile to microbes and thereby affords a low risk of microbial contamination.

A still further object of the present invention is to provide a relatively simple and effective in vitro method of evaluating the efficacy of topical skin barriers in protecting patients' skin from moisture and waste, and in their adhesion to skin.

In accordance with basic aspects of the present invention, a topical skin barrier for protecting and promoting healing of skin, and for providing comfort to a patient, comprises a semi-solid hydrocarbon, a water-absorbing compound, and a pain relief agent. The topical skin barrier effectively adheres to skin, affords protection from moisture and waste, provides transparency in use, and is anhydrous and therefore is preservative-free. Further in accordance with the invention are methods of in vitro evaluation of (i) a composition's protection from moisture and waste, and (ii) a composition's adhesion to skin.

DETAILED DESCRIPTION OF THE INVENTION

Figure 1:
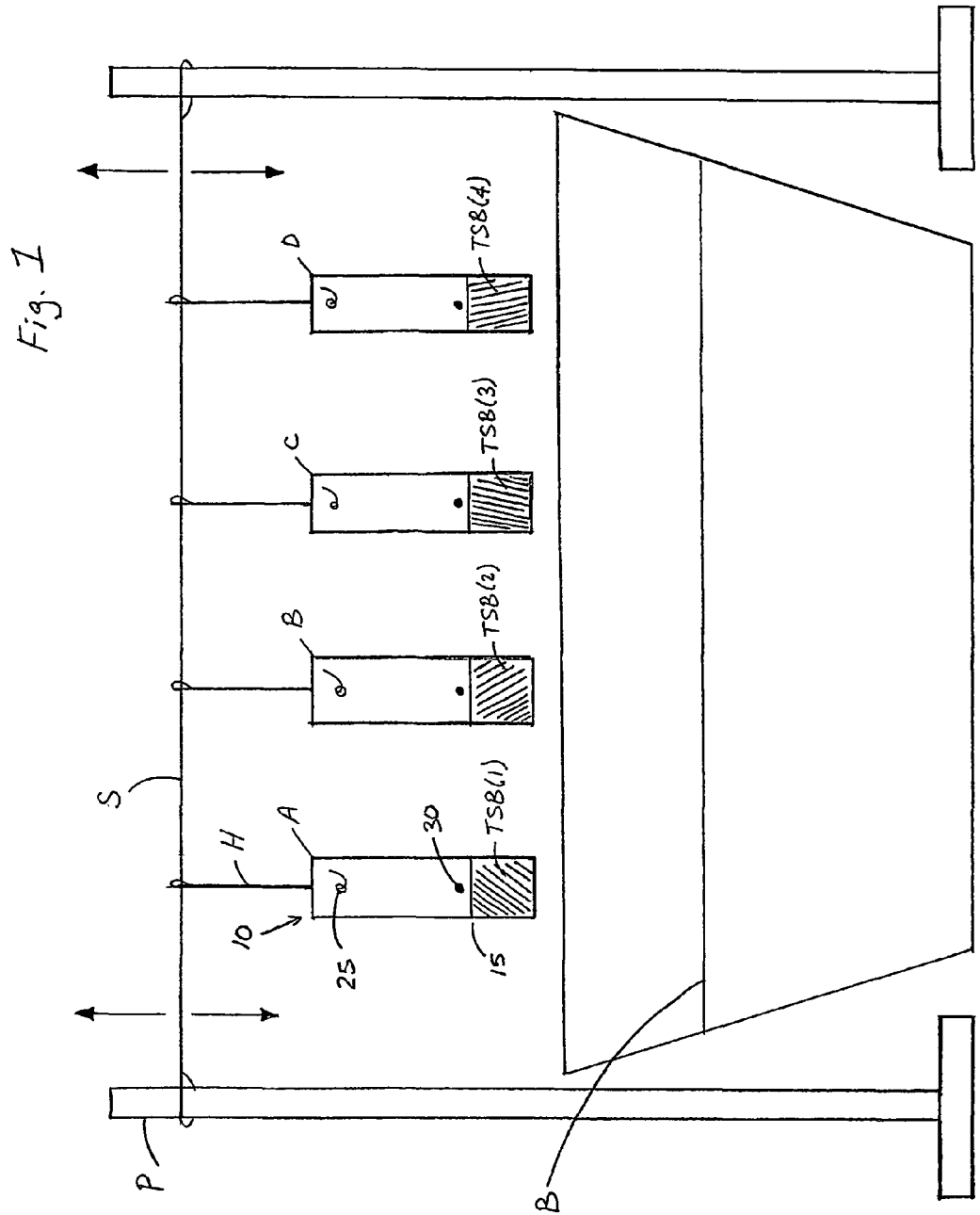
FIG. 1 is an illustration of a method for evaluating the efficacy of topical skin barriers in protecting patients' skin from moisture and waste, being prepared for use in accordance with the present invention.

As used here throughout, the term "water-absorbing compound" is intended to include any suitable compound such as, for example, (i) cellulose gum, whether identified as water-absorbing or otherwise, (ii) carboxymethylcellulose, commonly referred to as "CMC" and which is commercially available, for example, as BLANOSE® brand water soluble polymer from Hercules Incorporated of Wilmington, Del., (iii) karaya gum, and even (iv) specific brands of superabsorbent polymers such as WATER LOCK® G-430 and WATER LOCK® A-240, each being commercially available from Grain Processing Corporation of Muscatine, Iowa. Also as used here throughout, the terms "synthetic urine" or "suitable liquid" in the context of evaluation are intended to include any suitable liquid having properties similar to human urine such as, for example, URISUB™ synthetic urine for testing purposes from CST Technologies, Inc. of Great Neck, N.Y., and even a "no-rinse incontinence cleanser" such as PERI-WASH II® cleanser from Coloplast A/S of Denmark.

In development of the topical skin barriers of the present invention, several experimental compositions were formulated. These are presented as the following Examples 1-10.

EXAMPLE 1

25.0 grams of karaya gum is added to 74.5 grams of melted petrolatum. The two are mixed with a spatula. 0.5 grams of tocopheryl acetate is added and the mixture is spatulated and cooled to room temperature. This mixture adheres well in the presence of synthetic urine and provides a good barrier to moisture. However, the mixture is dark in color due to the karaya gum.

EXAMPLE 2

25.0 grams of cellulose gum is added to 74.5 grams of melted petrolatum. The two are mixed with a spatula. 0.5 grams of tocopheryl acetate is added and the mixture is spatulated and cooled to room temperature. This mixture adheres well in the presence of synthetic urine and provides a better moisture barrier than example 1. The mixture is lighter in color than example 1 but is still slightly dark.

EXAMPLE 3

25.0 grams of WATER LOCK® G-430 superabsorbent polymer is added to 74.5 grams of melted petrolatum. The two are mixed with a spatula. 0.5 grams of tocopheryl acetate is added and the mixture is spatulated and cooled to room temperature. This mixture does not adhere well in the presence of synthetic urine.

EXAMPLE 4

25.0 grams of WATER LOCK® A-240 superabsorbent polymer is added to 74.5 grams of melted petrolatum. The two are mixed with a spatula. 0.5 grams of tocopheryl acetate is added and the mixture is spatulated and cooled to room temperature. This mixture does not adhere well in the presence of synthetic urine.

EXAMPLE 5

25.0 grams of cellulose gum is added to 74.0 grams of melted petrolatum. The two are mixed with a spatula. 1.0 gram of zinc oxide is added and the mixture is spatulated and cooled to room temperature. This mixture adheres well in the presence of synthetic urine and provides a good moisture barrier. The color is more appealing than examples 1 or 2.

EXAMPLE 6

25.0 grams of cellulose gum is added to 73.0 grams of melted petrolatum. The two are mixed with a spatula. 2.0 grams of dimethicone is added and the mixture is spatulated and cooled to room temperature. This mixture adheres well in the presence of synthetic urine and provides a good moisture barrier. The dimethicone gives a mixture that is easier to spread.

EXAMPLE 7

25.0 grams of cellulose gum is added to 72.0 grams of melted petrolatum. The two are mixed with a spatula. 1.0 gram of zinc oxide and 2.0 grams of dimethicone are added and the mixture is spatulated and cooled to room temperature. This mixture adheres well in the presence of synthetic urine and provides a good moisture barrier. It is easy to spread and has an appealing color.

EXAMPLE 8

25.0 grams of cellulose gum is added to 72.5 grams of melted petrolatum. The two are mixed with a spatula. 0.5 grams of tocopheryl acetate and 1.0 gram of dimethicone are added and the mixture is spatulated and cooled to room temperature. This mixture adheres well in the presence of synthetic urine and provides a good moisture barrier. It is easy to spread.

EXAMPLE 9

25.0 grams of cellulose gum is added to 73.5 grams of melted petrolatum. The two are mixed with a spatula. 1.0 gram of zinc oxide and 0.5 gram of tocopheryl acetate are added and the mixture is spatulated and cooled to room temperature. This mixture adheres well in the presence of synthetic urine and provides a good moisture barrier. It has an appealing color.

EXAMPLE 10

25.0 grams of cellulose gum is added to 71.5 grams of melted petrolatum. The two are mixed with a spatula. 1.0 gram of zinc oxide, 0.5 gram of tocopheryl acetate, and 2.0 grams of dimethicone are added and the mixture is spatulated and cooled to room temperature. This mixture adheres well in the presence of synthetic urine and provides a good moisture barrier. It is easy to spread and has an appealing color.

The foregoing examples are presented in tabular form as follows (amounts are expressed in grams):

|  | Ex. 1 | Ex. 2 | Ex. 3 | Ex. 4 |
|---|---|---|---|---|
| Petrolatum | 74.5 | 74.5 | 74.5 | 74.5 |
| Karaya gum | 25.0 | — | — | — |
| Cellulose gum | — | 25.0 | — | — |
| WATER LOCK ® G-430 | — | — | 25.0 | — |
| Tocopheryl acetate | 0.5 | 0.5 | 0.5 | 0.5 |
| WATER LOCK ® A-240 | — | — | — | 25.0 |

|  | Ex. 5 | Ex. 6 | Ex. 7 |
|---|---|---|---|
| Petrolatum | 74.0 | 73.0 | 72.0 |
| Cellulose gum | 25.0 | 25.0 | 25.0 |

-continued

|  | | | |
|---|---|---|---|
| Zinc oxide | 1.0 | — | 1.0 |
| Dimethicone | — | 2.0 | 2.0 |

|  | Ex. 8 | Ex. 9 | Ex. 10 |
|---|---|---|---|
| Petrolatum | 72.5 | 73.5 | 71.5 |
| Cellulose gum | 25.0 | 25.0 | 25.0 |
| Tocopheryl acetate | 0.5 | 0.5 | 0.5 |
| Dimethicone | 2.0 | — | 2.0 |
| Zinc oxide | — | 1.0 | 1.0 |

It is to be understood that the foregoing Examples 1-4 have been presented as test results in development of the instant invention, while Examples 5-10 specifically serve as preferred or exemplary embodiments of the invention. Also, the phrase "appealing color" in the examples is intended to mean an appealing or subjectively aesthetic quality; additionally, "appealing color" is intended to include "detectable transparency" as aforementioned.

It is to be appreciated from the foregoing disclosure that the present invention satisfies the long-felt needs for a substantially transparent, anhydrous, topical skin barrier for general skin care which (i) is not limited in application to a specific area of a patient's body, (ii) may optionally include an antifungal, (iii) adheres well to skin and provides a good barrier in an environment of moisture and waste, and (iv) has detectable transparency. The present invention, therefore, may be further characterized, for example, as performing at least as satisfactorily as the prior CRITIC-AID® Paste from Coloplast A/S of Denmark.

Although not presented in Examples 1-10 above, further discoveries have been made relative to development of an antifungal property in the topical skin barriers of the present invention. The addition of a suitable antifungal, such as, for example, miconazole nitrate or clotrimazole, is desirable in some instances because the aforedescribed skin maladies are often susceptible to fungal infections. In this regard, it has been further discovered that such addition of a suitable antifungal gives an unexpected, additional result of an enhanced moisture and waste barrier property in a given formulation of the present invention. In a preferred, exemplary embodiment, utilization of miconazole nitrate in a range by weight from about 1.5% to about 2.5% alleviates a need for a material (e.g., zinc oxide) which lightens a coloration appearance of a given formulation. As an alternative clotrimazole may be substituted for miconazole nitrate, in a range by weight from about 0.5% to about 2.0%. Specifically, it has been found that the addition of miconazole nitrate or clotrimazole in such proportions inherently provides an appealing subjectively aesthetic quality along with detectable transparency.

Additionally, and although again not presented in Examples 1-10 above, it has been discovered that the topical skin barriers of the present invention may advantageously include a pain relief agent for patient comfort. The addition of a suitable pain relief agent, such as, for example, dibucaine, lidocaine, benzocaine, betamethasone, or tetracaine, in a range by weight from about 0.25% to about 20.0% depending upon the particular agent chosen as recognized by those in the medical or pharmaceutical arts, is desirable in some instances because the aforedescribed skin maladies may be painful.

It is to be recognized by those skilled in the medical or pharmaceutical arts that the topical skin barrier of the present invention may be properly characterized as being anhydrous, which is known to be hostile to microbes. Such an environment provided by the present invention would, therefore, advantageously afford a low risk of microbial contamination. Consequently, it is to be particularly noted, the various alternative compositions of the present invention do not require the addition of a preservative. Accordingly, the present invention may be properly characterized as being preservative-free.

In development of further preferred or exemplary embodiments of the present invention, it was recognized that utilization of an antifungal often occurs in an unpleasant odor-producing fungal environment. Therefore, it may be desirable to add an odor control agent to a given formulation of the invention, in a range by weight from about 0.1% to about 10.0%. A suitable odor control agent could be virtually any compatible, commercially available fragrance or deodorizer such as, for example, ORDENONE® brand deodorizer from Belle-Aire Fragrances, Inc., of Mundelein, Ill.

Figure 2:
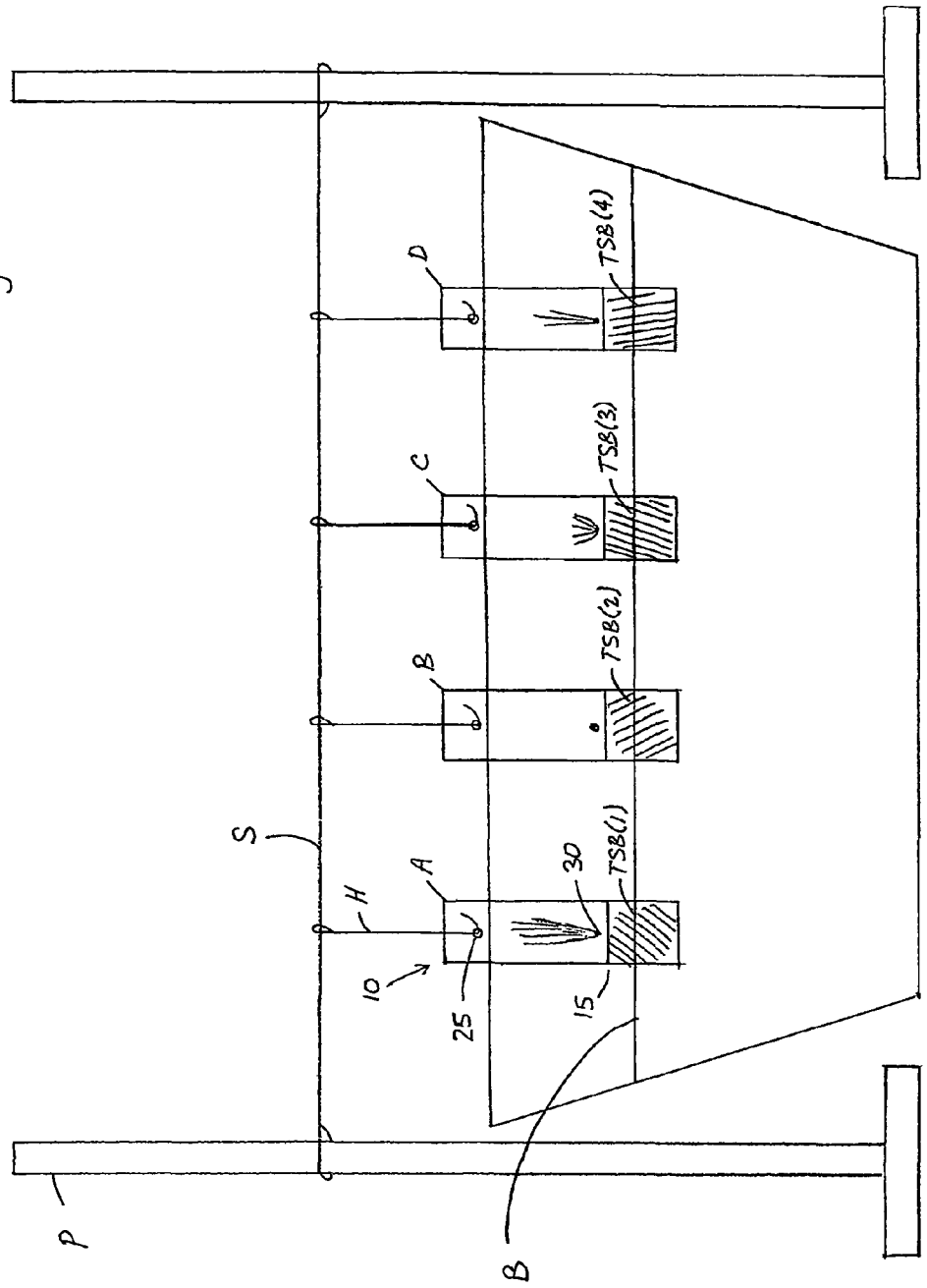
FIG. 2 is a depiction of the method of FIG. 1 during use.

Turning, now, to FIGS. 1 and 2, there shown is a exemplary in vitro method of evaluating the efficacy of topical skin barriers in protecting skin from moisture and waste, further in accordance with the present invention. The method was developed in response to rather complex evaluation protocols involving, for example, rolled filter paper as disclosed in Shah, et al., *Evaluation of Moisture Penetration Through Skin Protectant Barriers by Paper Chromatography*, Adv. Wound Care p. 20-21, 25, and 27 (July-August, 1995).

In general, testing has shown that an understanding of barrier properties of compositions may be gained from such simple devices as filter material, a synthetic urine bath, and a stopwatch. For instance, a small amount of a selected composition can be coated onto the filter material and immersed directly into a bath for a specified period of time. Many prototypes can be studied by this simple method to establish optimum moisture and waste barrier properties. In a specific exemplary embodiment of such an in vitro method of evaluating protection from moisture and waste, and with particular reference to FIG. 1, filter material 10 is cut into strips (A-D, as shown) measuring about 5.25" by about 0.50". The "filter material" may be any suitable filter paper such as, for example, WHATMAN® brand #4 filter paper from Whatman Paper Limited of the United Kingdom. Using a pencil, a line is drawn about 0.50" from the material's bottom edge (at 15). A small hole 25 is made near a top center portion of the strip of material 10. Hole 25 is provided to hang the strip on a horizontally-positionable string S over a suitable liquid serving as synthetic urine bath B by way of posts P. A dot 30 of water soluble ink is then placed just above line 15, which is utilized in tracking moisture migration as will be described. Each strip A-D of material 10 is then evenly coated on both sides thereof with, respectively, approximately 0.1 g. of a separate topical skin barrier to be respectively evaluated (as shown, TSB(1)-TSB(4)). Each coating corresponds, as shown, to a portion of material 10 between line 15 and its bottom edge. With each strip A-D of material 10 so prepared, they are then suspended from string S via hangers H at holes 25 so that topical skin barriers TSB(1)-(4) may be simultaneously, or nearly so, submerged in bath B of synthetic urine at a temperature of about 37C by way of lowering string S at each post P. In this manner, it is to be appreciated that each strip A-D of filter material 10 including the respective coatings of barriers TSB(1)-(4) may be maintained at a selected depth in bath B not to exceed lines 15. Strips A-D are maintained in such immersed positions for about 2 hours. As shown in FIG. 2, it can be helpful to monitor the progress of the synthetic urine migrating up strips A-D with respect to lines 15 at intermediate elapsed times (e.g., 30 minutes and 1 hour, etc.). After about 2 hours strips A-D are removed from bath B. Respective distances of moisture migration as evidenced by an extent of vertical transport of ink from dot 30, up each strip of filter material 10 relative to lines 15, are then measured. Those of ordinary skill in the art will appreciate that such distances are indicative of the efficacy of the respective topical skin barriers in protecting skin from moisture and waste, and may be conveniently expressed as a rate of penetration in mm/2hr. Of course, the aforedescribed evaluation method may be carried out with virtually any number of strips A-(N) of material 10, for, respectively, any number of different topical skin barriers TSB(1)-(N) to be evaluated with respect to one another.

Finally, although not specifically illustrated but with analogous continued reference to the drawings, the present invention also provides an in vitro method of evaluating the efficacy of topical skin barriers in their adhesion to skin. This evaluation method, in accordance with another aspect of the present invention, shows that as in the aforedescribed barrier property evaluation, an understanding of efficacy of adhesion in a particular topical skin barrier may be gained from utilization of simple devices. In this method, a stainless steel plate is substituted for each strip of material 10, and bath B is provided as a sonication bath of synthetic urine (i.e., a bath of synthetic urine intentionally agitated by way of ultrasonic waves. Using a suitable marker, a line is drawn about 4 cm. from the plate's bottom edge. A small hole is made near a top center portion of the plate, with the hole providing means to hang the plate on a horizontally-positionable string over the sonication bath by way of posts. Each plate is then evenly coated on one side thereof with, respectively, approximately 1.0 g. of a separate topical skin barrier to be respectively evaluated, corresponding to a portion of the plate between the line and its bottom edge. Each plate is then suspended from the string via a hanger engaging the hole so that a given topical skin barrier coated on each plate may be simultaneously, or nearly so, submerged in the sonication bath of synthetic urine at a temperature of about 37C by way of lowering the string as aforedescribed. In this manner, it is to be appreciated that each plate including the respective topical skin barrier coatings are equally maintained at a selected depth in the bath exceeding the lines drawn on each plate. The plates are maintained in such immersed positions for about 5 minutes, at which time they are removed from the bath and respective adhesions of the various topical skin barriers are compared to one another. Those of ordinary skill in the art will appreciate that such comparisons are indicative of the efficacy of the topical skin barriers to remain adhered to skin in a dynamic patient environment where the presence of moisture and waste is typical. Of course, as with the aforedescribed barrier evaluation method, this adhesion evaluation method may be carried out with any number of plates for, respectively, any number of different topical skin barriers to be evaluated with respect to one another.

From the aforedescribed evaluation methods of the present invention, it was found that moisture and waste barrier properties, and also adhesion properties, were noticeably affected by incorporation of semi-solid hydrocarbon and cellulose gum as apparent by study of the foregoing Examples 1-10. In addition, it was discovered that a specific type of cellulose gum is critical to performance of the topical skin barriers of the present invention, with a combination of petrolatum and specific grades of cellulose gum providing desired barrier and adhesion properties better than other combinations. In particular, an optimum cellulose gum has a "degree of substitution" of 0.80-0.95 and a "fine" particle size. Generally, a lower degree of substitution results in better moisture absorption and hence better adhesion; however, too low a degree of substitution actually absorbs moisture too well and thereby degrades adhesion.

While the present invention has been particularly shown and described with reference to the accompanying figures and specification, it will be understood however that other modifications thereto are of course possible; and all of which are intended to be within the true spirit and scope of the present invention. It should be appreciated that components, dimensions, elapsed times, and other particulars of exemplary embodiments of the invention aforedescribed may be substituted for others which are suitable for achieving desired results, or that various accessories may be added thereto. It is also to be understood in general that any suitable alternatives may be employed to provide the topical skin barriers and their evaluation methods of the present invention.

It is to be noted that terms used here throughout are intended to have their usual, customary, and ordinary meanings, unless another is specified. In particular, it is to be understood that the following terms include, but are not limited to, the following associated meanings: "comfort" means a feeling of relief from unpleasant physical sensations; "protecting" means covering or shielding from exposure, injury, or destruction; "promoting healing" means contributing to, or advancing, a healing process; and "effective adhesion" means being operative to provide adequate adhesion.

Lastly, of course, the choice of compositions, sizes, and strengths of various aforementioned elements of the products and methods of the present invention are all a matter of design choice depending upon intended uses thereof.

Accordingly, these and other various changes or modifications in form and detail of the present invention may also be made therein, again without departing from the true spirit and scope of the invention as defined by the appended claims.

What is claimed is:

1. A topical skin barrier comprising:
   in a range by weight from about 25.0% to about 90.0%, a petrolatum;
   in a range by weight from about 5.0% to about 50.0%, a cellulose gum having a degree of substitution between 0.80-0.95; and
   one of miconazole nitrate and clotrimazole added to said topical skin barrier;
   wherein said topical skin barrier is substantially transparent to permit visual observation of skin under said topical skin barrier.

2. The topical skin barrier of claim 1 further comprising, in a range by weight from about 0.1% to about 20.0%, an agent which (i) improves application slip and (ii) promotes ease of removal of the topical skin barrier from skin to which it has been applied.

3. The topical skin barrier of claim 1, further comprising, in a range by weight from about 0.1% to about 5.0% tocopheryl acetate.

4. The topical skin barrier of claim 1, wherein said petrolatum is white petrolatum.

5. The topical skin barrier of claim 2, wherein said agent is dimethicone.

6. The topical skin barrier of claim 1, wherein said pain reliever is selected from the group consisting of dibucaine, lidocaine, benzocaine, betamethasone, and tetracaine.

7. A topical skin barrier comprising:
   in a range by weight from about 25.0% to about 90.0%, a semi-solid hydrocarbon;
   in a range by weight from about 5.0% to about 50.0%, a cellulose gum having a degree of substitution between 0.80-0.95; and in a range by weight from about 0.5% to about 2.5%, an antifungal agent added to said topical skin barrier to enhance moisture barrier and waste barrier of said topical skin barrier;

wherein said topical skin barrier has effective adhesion to skin and is substantially transparent to permit visual observation of skin under said topical skin barrier.

8. The topical skin barrier of claim 7, further comprising, in a range by weight from about 0.1% to about 20.0% dimethicone.

9. The topical skin barrier of claim 7, further comprising, in a range by weight from about 0.1% to about 5.0% tocopheryl acetate.

10. The topical skin barrier of claim 7, wherein said semi-solid hydrocarbon is selected from the group consisting of petrolatum and white petrolatum.

11. The topical skin barrier of claim 7, wherein said cellulose gum is carboxymethylcellulose.

12. The topical skin barrier of claim 7, wherein said antifungal agent is selected from the group consisting of miconazole nitrate and clotrimazole.

13. The topical skin barrier of claim 7, further comprising:
a pain reliever in a range by weight from about 0.25% to about 20.0% selected from the group consisting of dibucaine, lidocaine, benzocaine, betamethasone, and tetracaine.

14. The topical skin barrier of claim 1, wherein said topical skin barrier is an anhydrous topical skin barrier.

15. The topical skin barrier of claim 1, further comprising:
in a range by weight from about 0.25% to about 20.0%, a pain relief agent.

* * * * *